United States Patent [19]

Holroyd

[11] 4,146,030

[45] Mar. 27, 1979

[54] CRYOSURGICAL INSTRUMENT

[75] Inventor: Joseph A. Holroyd, Westford, Mass.

[73] Assignee: Dynatech Corporation, Burlington, Mass.

[21] Appl. No.: 754,833

[22] Filed: Dec. 27, 1976

[51] Int. Cl.² ............................................. A61B 17/36
[52] U.S. Cl. .................................... 128/303.1; 62/293
[58] Field of Search .................... 128/303.1, 400, 401; 62/293

[56] References Cited

U.S. PATENT DOCUMENTS

| | | | |
|---|---|---|---|
| 3,512,531 | 5/1970 | Crump et al. | 128/303.1 |
| 3,536,075 | 10/1970 | Thomas, Jr. | 128/303.1 |
| 3,548,829 | 12/1970 | Reynolds et al. | 128/303.1 |
| 3,575,176 | 4/1971 | Crump et al. | 128/303.1 |
| 3,696,813 | 10/1972 | Wallach | 128/303.1 |
| 3,913,581 | 10/1975 | Ritson et al. | 128/303.1 |
| 3,993,075 | 11/1976 | Lisenbee | 128/303.1 |

Primary Examiner—Lee S. Cohen
Attorney, Agent, or Firm—Cesari and McKenna

[57] ABSTRACT

An improved defrostable cryosurgical instrument has a unitary in-line valve assembly that permits the assembly to be contained right in the instrument itself without making the instrument unduly large, heavy or upsetting its balance. By a fingertip control right in the instrument itself, the valve assembly can be controlled to route refrigerant through the instrument's tip to operate the instrument in a freeze mode, a defrost mode and to turn the instrument off, while simultaneously depressurizing the tip.

8 Claims, 33 Drawing Figures

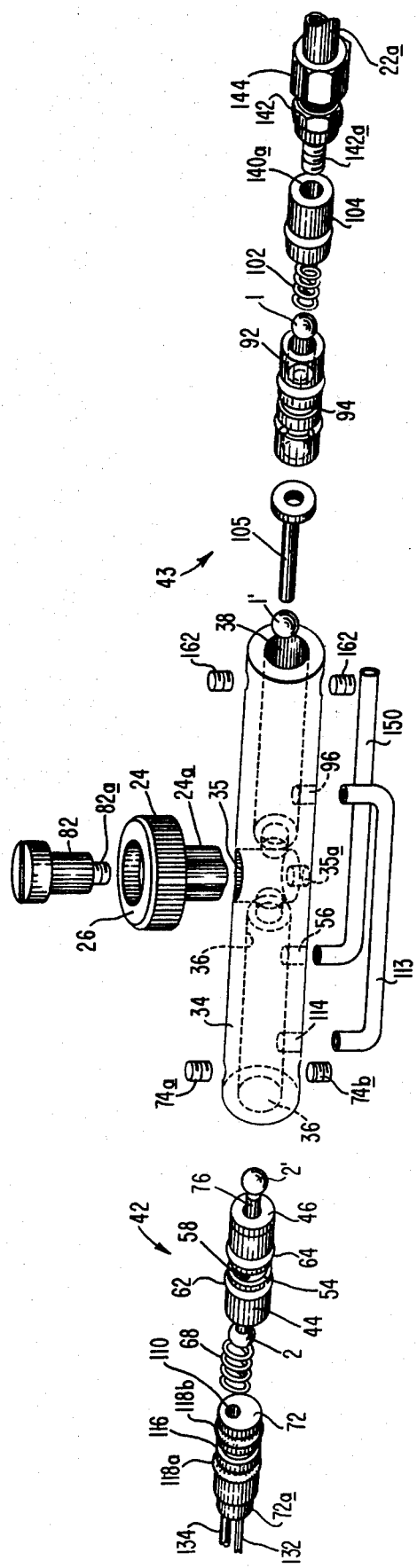
FIG. 3
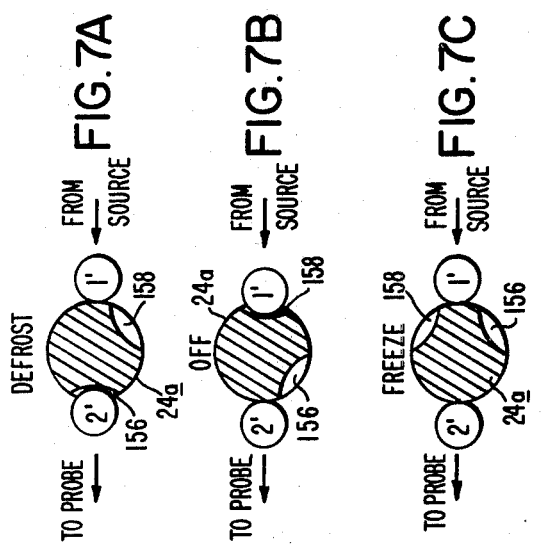
FIG. 7A
FIG. 7B
FIG. 7C
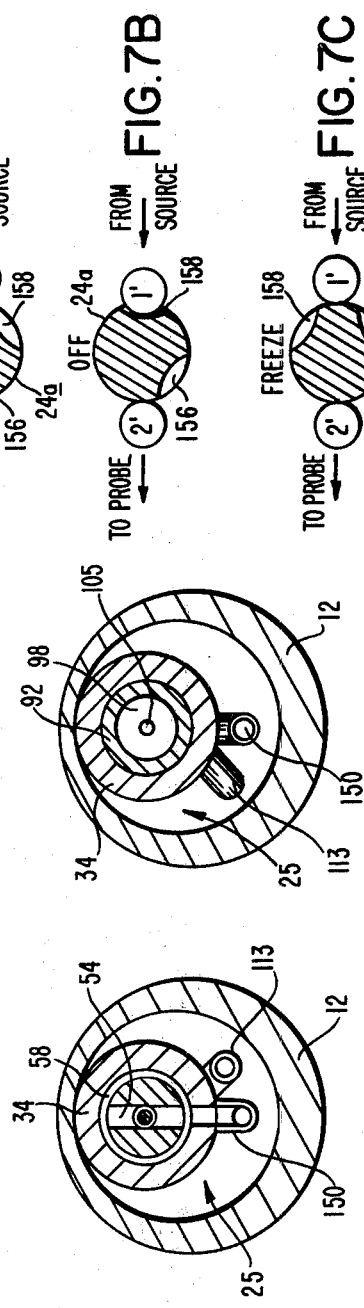
FIG. 6
FIG. 5
FIG. 4

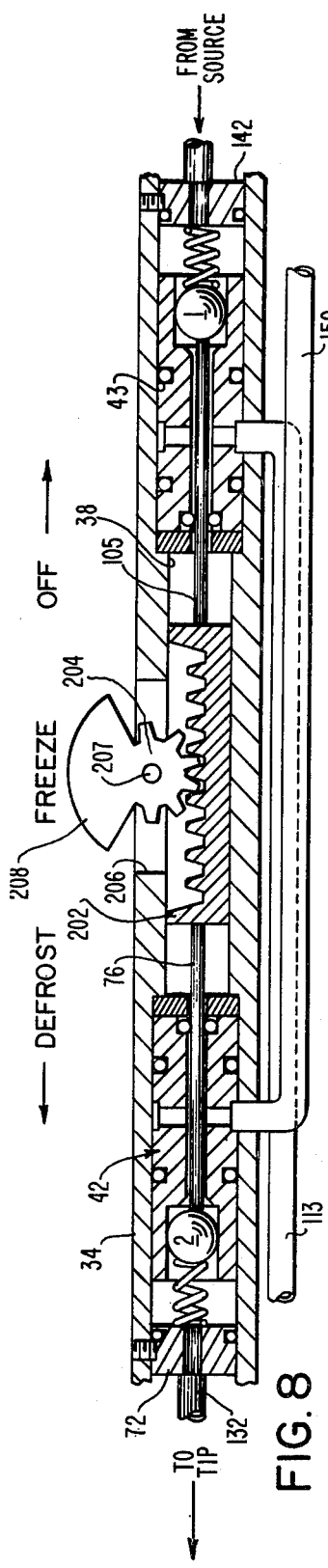
FIG. 8
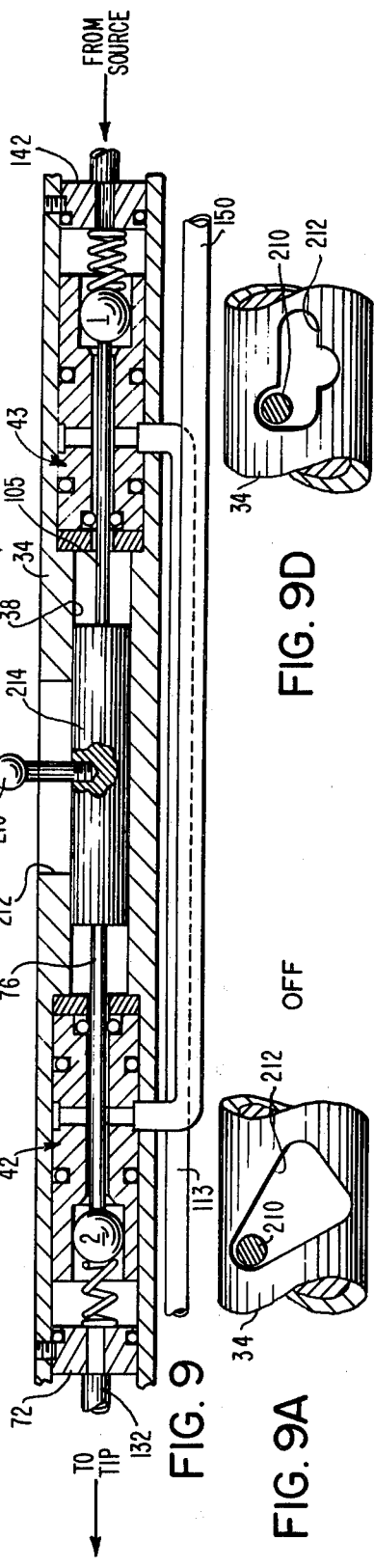
FIG. 9
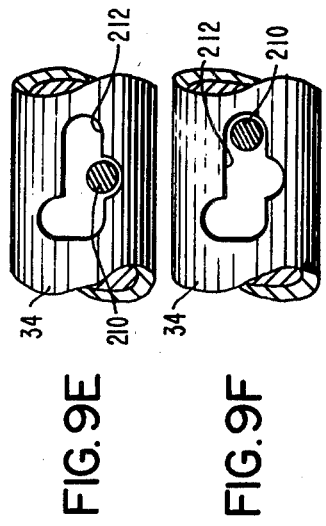
FIG. 9D
FIG. 9E
FIG. 9F
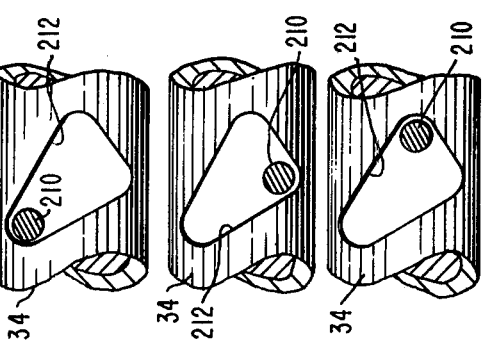
FIG. 9A
FIG. 9B
FIG. 9C

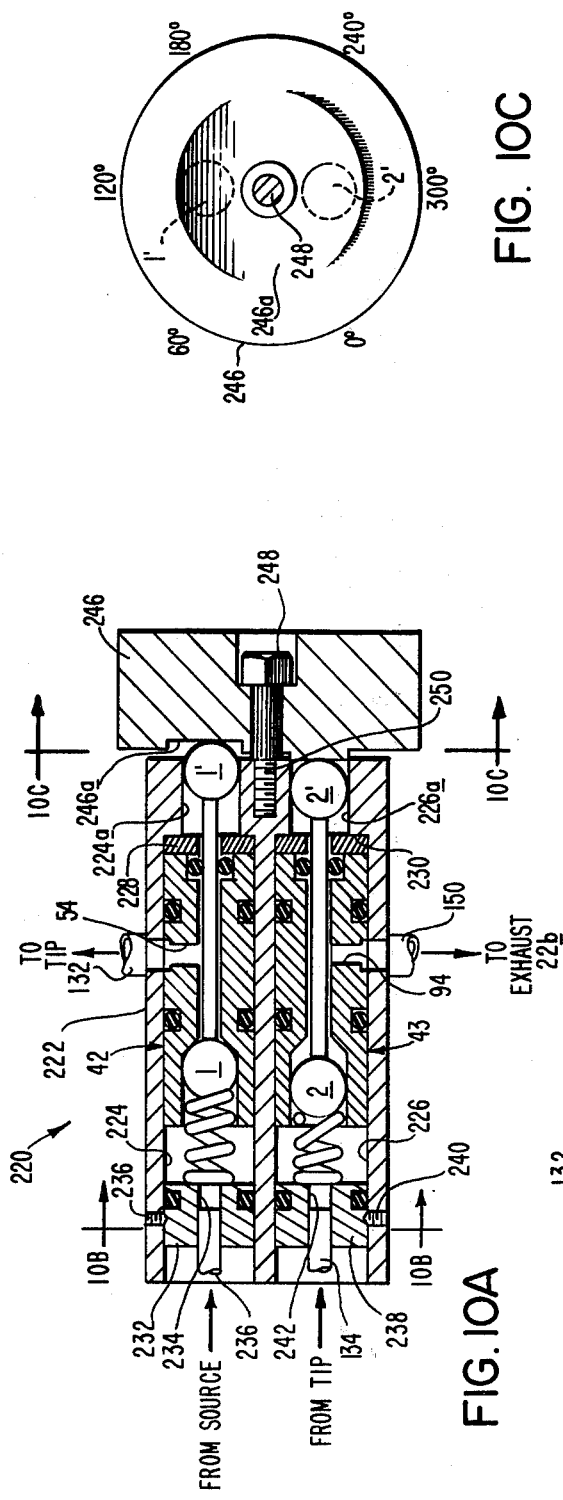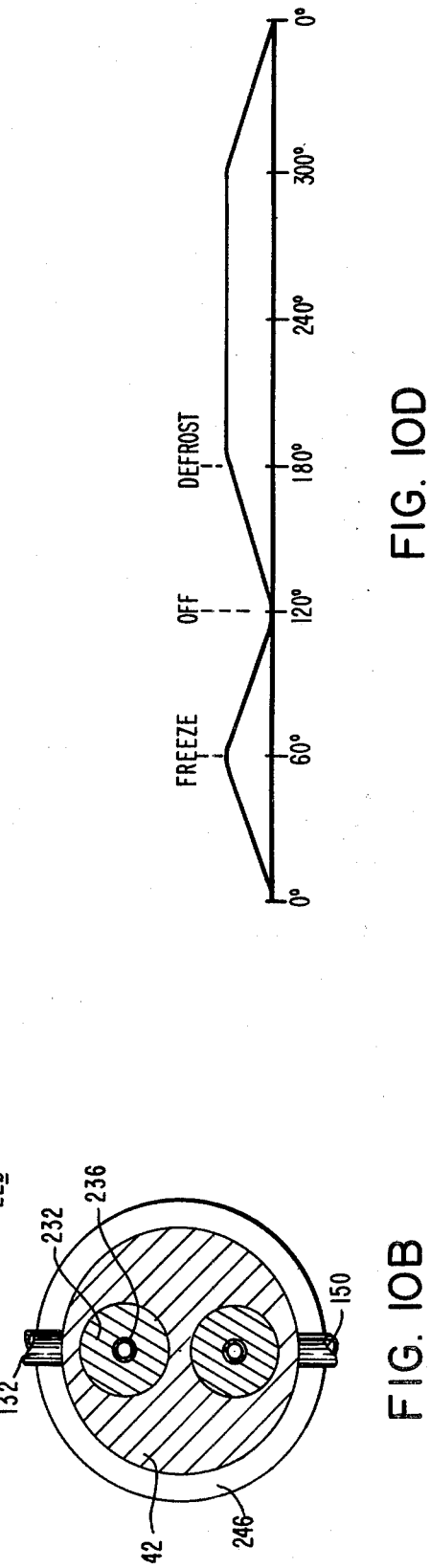
FIG. 10A
FIG. 10B
FIG. 10C
FIG. 10D

DEFROST

OFF

FREEZE

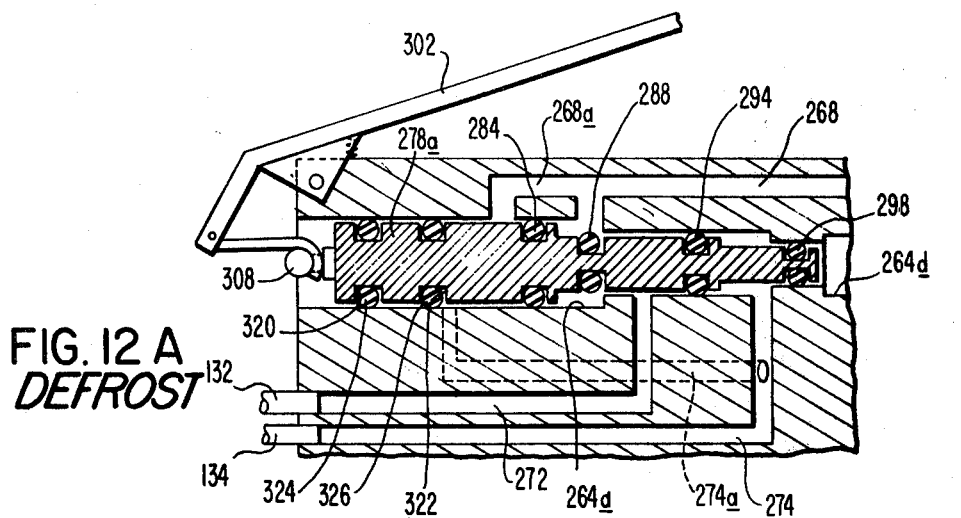
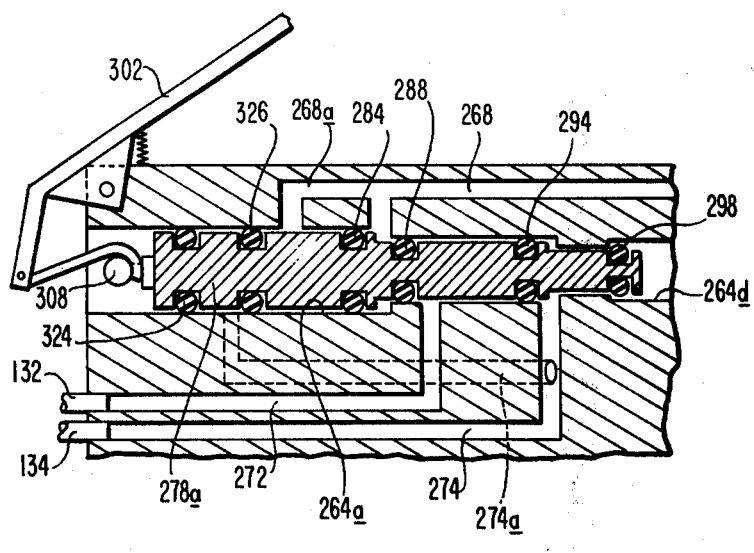
FIG. 12 A DEFROST
FIG. 12B OFF
FIG. 12C FREEZE

CRYOSURGICAL INSTRUMENT

BACKGROUND OF THE INVENTION

This invention relates to a cryosurgical instrument. It relates more particularly to an instrument of this type having a non-electric defrost capability. In such equipment, gaseous refrigerant is conducted via a restriction to the hollow working tip of the instrument whereby tissue in contact with the tip becomes frozen. Thereafter the tip may be warmed to facilitate its separation from the tissue by providing warm refrigerant at the hollow working tip of the instrument.

Several non-electrical methods have been proposed for reheating the working tips of similar instruments. One such method is disclosed in U.S. Pat. No. 3,696,813 and involves restricting or completely closing the exhaust passage from the tip so that refrigerant fluid, still flowing through the restriction raises the pressure within the working tip. Resultantly the gaseous refrigerant begins to condense on the cold surfaces of the tip, the latent heat of condensation thereby warming the tip sufficiently to permits its separation from the tissue.

In another cryosurgical instrument, the cooling of the hollow working tip of the instrument is provided by unseating a flow valve element in the return line located downstream from the tip and simultaneously forming a restrictive orifice at the inlet to the tip by contacting an orifice seat with a moveable conduit. Refrigerant then flows from the source through the orifice and exhausts through the unseated downstream valve. Warming of the tip is accomplished by seating the downstream valve element and simultaneously separating the moveable conduit from the orifice seat thus permitting refrigerant at ambient temperature to flood the hollow working tip.

Still another instrument of this type having a nonelectric defrost capability is described in U.S. Pat. No. 3,913,581. That instrument is similar to the first-mentioned one except that during the defrost mode of operation, the hollow tip of the instrument is pressurized from the source of refrigerant through a flow path separate from flow restricting inlet to the tip. In this type, the refrigerant is said to condense on the tip wall more rapidly thereby resulting in a more rapid warming of the tip during the defrost mode of operation.

These prior cryosurgical instruments having a defrost capability all have attendant disadvantages which militate against their wider use and application. More particularly, the instrument described in U.S. Pat. No. 3,696,813 has rather large valves which are mounted in the instrument itself resulting in a large gun-shaped probe that is quite unwieldy and appears threatening to some patients. On the other hand, the instrument having the flow valve in the probe that unseats, requires a moveable conduit and valving that are complex and therefore difficult and expensive to make on a consistently reliable basis. Finally, the instrument embodiments described in U.S. Pat. No. 3,913,581 all have hand or foot-operated valves separate from the instrument itself. Consequently they require separate consoles and extra high pressure hose lines making the overall systems more expensive and also more bulky and difficult to move about. There is no teaching in that patent how the disclosed valve arrangements could be incorporated into the instrument itself without making it large, unbalanced in speculum and generally difficult for the doctor to hold and manipulate during a prolonged or delicate surgical procedure.

SUMMARY OF THE INVENTION

Accordingly, it is the object of the present invention to provide a defrostable-cryosurgical instrument that is relatively compact, and easy to manipulate even for a prolonged period.

Another object of the invention is to provide a cryosurgical instrument of this type all of whose valving is contained in the instrument handle, yet which is lightweight and well balanced.

Yet another object of the invention is to provide a cryosurgical instrument of this type which is relatively easy and inexpensive to make and maintain.

Still another object of the invention is to provide a cryosurgical instrument which can be switched between its various modes of operation by means of a single, readily accessible finger tip control right on the instrument itself.

Other objects will, in part, be obvious and will, in part, appear hereinafter.

The invention accordingly comprises the features of construction, combination of elements and arrangement of parts which will be exemplified in the following detailed description, the scope of the invention being indicated in the claims.

Briefly, the present cryosurgical instrument is shown in the form of a relatively lightweight, hand-held probe. The probe is adapted to be connected via a flexible hose directly to a source of a suitable pressurized refrigerant such as gaseous nitrous oxide or carbon dioxide.

The probe has a thin, elongated handle and a hollow thermally conductive tip projecting from the distal end of the handle. Refrigerant from the source is conducted via the hose to a compact, unitary, in-line pneumatic valve assembly inside the handle. A restricted first conduit extends from the assembly into the hollow probe tip.

During the freeze mode of operation, the valve assembly connects this first conduit to the refrigerant source. Refrigerant issuing from the end of the conduit expands into the hollow tip, cooling in the process and thereby cooling the tip wall. Refrigerant is conducted out of the hollow tip via an unrestricted second conduit leading to the valve assembly, which thereafter directs the spent refrigerant to the atmosphere via an exhaust line in the flexible hose.

When the instrument is turned off, the valve assembly interrupts the flow of refrigerant from the source to the tip of the instrument while establishing communication between the hollow tip and the second conduit leading to the atmosphere in order to depressurize the tip to relieve the stress on the tip and to facilitate changing tips. For example, a spray tip to be described later can be used in lieu of the hollow tip.

The instrument's valve assembly may assume different specific forms depending upon the routing of the refrigerant through the instrument during its defrost operating mode. In one instrument embodiment, during the defrost mode of operation the valve assembly maintains communication between the refrigerant source and the restricted first conduit extending into the probe tip. At the same time, the assembly closes the second conduit leading from the tip to the atmosphere thereby raising the pressure inside the hollow tip to the full source pressure causing the gaseous refrigerant to condense inside the tip and to give up its latent heat of vaporization to the tip walls. Whereupon the tip becomes warmed so that it is readily separated from the tissue to which it was adhered. Instruments of this general type which warm the tip by preventing refrigerant from exhausting from the tip can exist in several species to be described later.

In another general type of cryosurgical instrument, during the defrost mode of operation the valve assembly routes refrigerant to the probe tip via the unrestricted second conduit and the assembly may also reduce or interrupt flow of refrigerant from the tip via the first conduit. Here also there is a buildup of pressure inside the tip which causes the refrigerant to condense and thereby warm the tip as described above. Here also there may be several species within this general type of instrument which warms the tip by flooding it with source refrigerant through an unrestricted conduit leading to the tip.

In a third type of instrument, the valve assembly controls the warming of the tip by reversing the flow of refrigerant through the probe. In other words, during the defrost mode, the valve assembly conducts refrigerant under source pressure to the probe tip via the unrestricted second conduit and exhausts refrigerant from the tip to the atmosphere via the restricted first conduit. Since the source refrigerant is at room temperature and is flowed through the tip without suffering a pressure drop, the probe tip is warmed rapidly to room temperature.

In all of the instrument embodiments, when the probe is turned off, the valve assembly interrupts the flow of refrigerant from the source to the tip and simultaneously connects the tip to the atmosphere so that the tip is depressurized to relieve stresses on the tip and to permit the tip to be changed without having to turn off the refrigerant at the source.

Although the valve assembly assumes different forms depending upon the routing of refrigerant through the instrument, in all cases the assembly is of unitary in-line construction and is composed of a minimum of moving parts. Furthermore, as compared with the multiple valves required on prior comparable instruments of this type, the assembly is relatively simple and therefore inexpensive to make. Further, it is rugged and reliable giving the overall instrument a relatively long useful life. Also the design of the valve assembly permits it to be incorporated into a relatively slim instrument handle so that the instrument has excellent balance in speculum and is easy to manipulate during difficult or prolonged surgical procedures.

BRIEF DESCRIPTION OF THE DRAWINGS

For a fuller understanding of the nature and objects of the invention, reference should be made to the following detailed description taken in connection with the accompanying drawings in which:

FIG. 3 is an exploded perspective view of major internal components of the FIG. 2 instrument;

FIGS. 4 to 6 are sectional views taken along lines 4—4, 5—5, 6—6 respectively in FIG. 2;

FIGS. 7A to 7C are diagrammatic views illustrating the three different operative positions of the instrument's control knob;

FIG. 8 is a view in medial section with parts in elevation showing a modified valve assembly for use in the FIG. 1 instrument;

FIG. 9 is a similar view of another valve assembly embodiment;

FIGS. 9A to 9F are diagrammatic views describing the operation of the FIG. 9 valve assembly;

FIG. 10A is a view like FIG. 8 showing still another valve assembly embodiment for use in instruments of this type;

FIG. 10B is a sectional view along line 10B-1023 in FIG. 10A;

FIG. 10C is an end view of the control knob of the FIG. 10A assembly;

FIG. 10D is a graphical diagram illustrating the operation of the FIG. 10A assembly;

FIGS. 12A to 12C are similar views of still another valve assembly embodiment;

DESCRIPTION OF THE PREFERRED EMBODIMENTS

Figure 1:
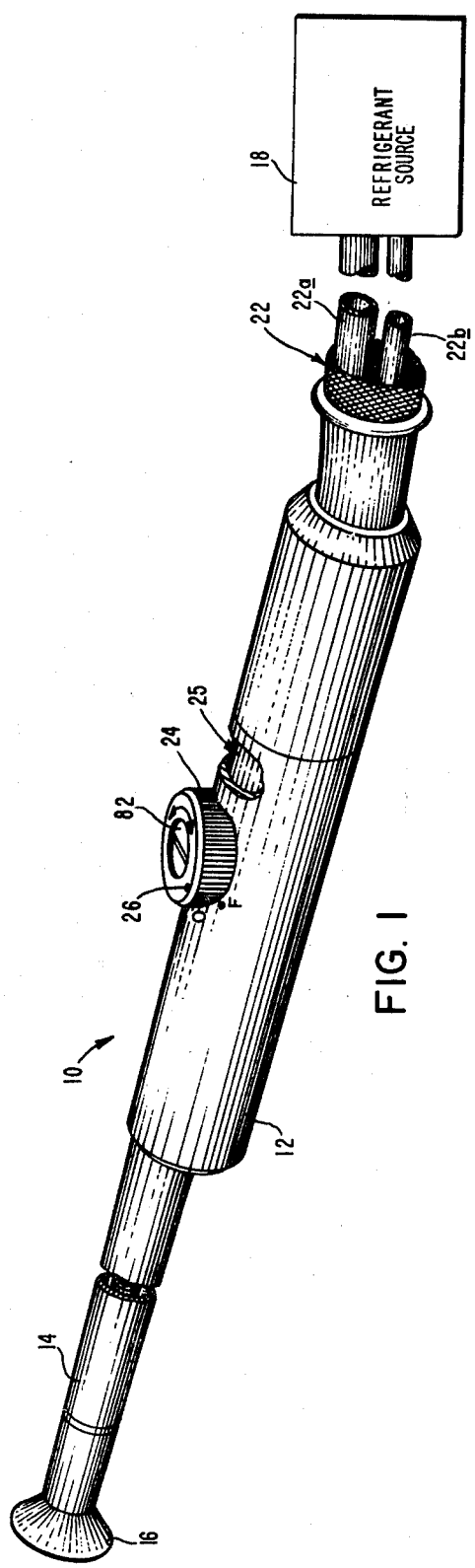
FIG. 1 is a diagrammatic view of a cryosurgical instrument made in accordance with this invention.

Referring first to FIG. 1 of the drawings, the subject probe shown generally at 10 has a long slim, generally cylindrical handle 12 molded of a suitable impact-resistant plastic. Projecting from the distal end of handle 12 is a long, cylindrical metal or plastic shroud 14 terminating in a hollow thermally conductive tip 16. Pressurized gaseous refrigerant such as nitrous oxide or carbon dioxide is conducted from a refrigerant source 18 to the instrument by way of a flexible pressure resistant hose 22 extending into the proximate end of handle 12.

Once the refrigerant source 18 is turned on, operation of the instrument 10 is controlled entirely by manipulating a knurled knob 24 on the instrument handle 12. More particularly, when the knob is positioned with the bench mark 26 on the knob aligned with handle 12, the instrument is turned off. In this condition, no refrigerant is conducted to the interior of tip 16 and the tip is vented to the atmosphere by way of hose 22. When the knob 24 is turned counter-clockwise to the FREEZE position, refrigerant is conducted from the source to the interior of tip 16. Whereupon the refrigerant entering the tip cools by expansion and the Joule-Thomson effect, cooling the tip walls in the process. The spent refrigerant is exhausted from the tip to the atmosphere by way of hose 22. When the knob 24 is turned clockwise from its OFF position, the instrument operates in its defrost mode. Now refrigerant at substantially room temperature is conducted to the interior of tip 16 thereby warming the tip to facilitate its detachment from the tissue to which it was adhered during the freeze mode of operation. Again, refrigerant is exhausted from the tip to the atmosphere by way of hose 22.

As will be seen presently, knob 24 controls a valve assembly 25 contained entirely within handle 12 that routes refrigerant to and from tip 16 so that the instrument 10 operates properly in the manner just described. The valve assembly 25 has a compact unitary construction so that it can be contained entirely within handle 12 without materially increasing the size of the handle over and above that which would be required in any event for the doctor to properly manipulate the instrument. In other words, as seen in FIG. 1, instrument 10 is relatively small and lightweight and is characterized by smooth, clean lines and excellent balance in speculum so that it can be manipulated easily by the doctor and does not present a threatening appearance to the patient. Even though the instrument is relatively small and lightweight, the single control knob 24 right on the instrument itself is all that the doctor requires to properly operate the instrument. He does not have to concern himself with controls on remote consoles or foot controls or remote relays as is the case with prior comparable instruments of this general type which might be of comparable size and weight.

Turning now to FIGS. 2 to 6, the valve assembly 25 is positioned in a cavity 32 between the ends of handle 12. In its embodiment, the assembly is arranged so that the tip 16 is warmed by blocking the exhaust of refrigerant from the tip. As such, assembly 25 comprises an elongated generally cylindrical valve manifold 34 made of brass or other suitable metal which can be machined easily. A diametric passage 35 is formed in manifold 34 intermediate its ends. Passage 35 extends almost all the way through the manifold with its interior end having a reduced diameter at 35a and being threaded. A pair of cylindrical bores 36 and 38 extend inward from the opposite ends of manifold 34 to passage 35. Moreover the inner end portions of those bores having reduced diameters at 36a and 38a forming annular shoulders 36b and 38b spaced equal distances from passage 35.

Figure 2:
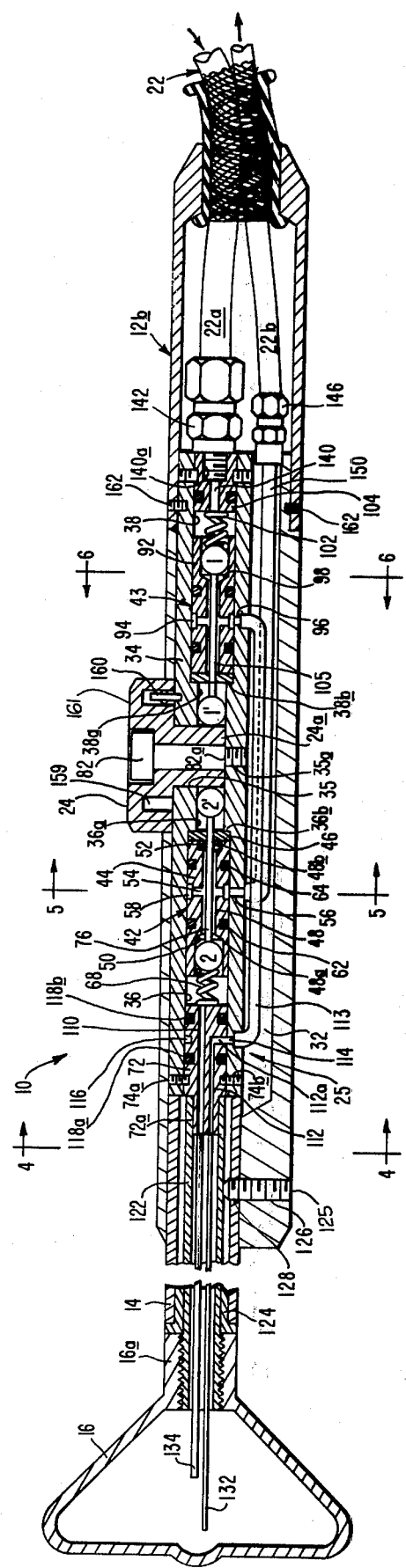
FIG. 2 is a view in medial section with parts in elevation showing the FIG. 1 instrument in greater detail.

Bores 36 and 38 contain valve structures indicated generally at 42 and 43. Since these structures are mirror images of one another, we will only describe the left hand structure 42 in detail. Structure 42 comprises an elongated cylindrical valve member 44 whose diameter is slightly less than that of bore 36 so that the member can be slid into the bore and fit snuggly therein with its inner end seating against shoulder 36b. Preferably a discoid gasket 46 is provided between the member 44 and the shoulder as best seen in FIG. 2. A relatively small diameter axial bore 48 extends the length of member 44. Also the outer end of bore 48 is counterbored at 48a, the shoulder between bore 48 and the counterbore 48a being beveled to form a valve seat 50. A shallower counterbore 48b of like diameter is formed at the inner end of member 44 for accommodating an O-ring 52.

A diametric passage 54 is formed in member 44 intermediate its ends which intersects passage 48. Passage 54 is intended to communicate with a port 56 in the side wall of manifold 34 when member 44 is properly seated against shoulder 36b. To assure proper communication between those passages for any radial orientation of member 44, there is a circumferential groove 58 around member 44 coincident with the mouths of passage 54. Also, circumferential grooves are formed in member 44 on opposite sides of passage 54 for accommodating O-rings 62 and 64 so that fluid cannot flow from the ends of passage 54 along the clearance space between member 44 and manifold 34.

Valve structure 42 also includes a valve ball 2 positioned in counterbore 48a arranged to seat against the valve seat 50 preventing fluid flow between the left-hand end of bore 36 and passage 48 in member 44. Ball 2 is biased against the valve seat 50 by a spring 68 that reacts against a cylindrical plug 72 positioned at the outer end of bore 36. Plug 72 is held in place within the bore by set screws 74a and 74b threaded through the opposite walls of manifold 34 so as to engage plug 72.

Ball 2 is unseated from seat 50 by means of a push rod 76 extending along bore 48 and projecting through gasket 46 and into the reduced diameter bore portion 36a in manifold 34. The inner end of push rod 76 bears against a ball 2'. Ball 2', in turn, bears against the stem 24a of knob 24 when the instrument is properly assembled. More particularly, as best seen in FIGS. 2 and 3, the knob stem 24a is sized to fit down into passage 35 in manifold 34 with its bottom resting against the shoulder adjacent the reduced diameter passage portion 35a. An axial opening is provided in knob 24 for accommodating a bolt 82 having a reduced diameter threaded end 82a which is turned down into the threaded passage portion 35a as shown in FIG. 2. When the knob 24 is properly seated, the spring 68 biases valve ball 2 toward its closed position and the ball, in turn, acts through push rod 76 to bias ball 2' against the knob stem 24a.

The valve structure 43 comprises identical elements including a valve member 92 having a diametric passage 94 communicating with a port 96 in the wall of manifold 34. A valve ball 1 is biased against a valve seat 98 in member 92 by a spring 102 which reacts against a plug 104 retained at the right end of bore 38. A push rod 105 extending axially through member 92 engages valve ball 1 at one end and a second ball 1' at its opposite end. The latter ball also bears against the knob stem 24a at a point thereon directly opposite the point of engagement therewith by ball 2'.

As best seen in FIG. 2, plug 72 at the left-hand end of the valve assembly has an axial passage 110. A second parallel passage 112 extends from the outer or left-hand end of plug 72 approximately two-thirds along its length where it communicates with a radial passage 112a and thereby with a port 114 in the side wall of manifold 34. A pipe 113 is connected between port 114 and port 96 adjacent valve structure 43. Also a circumferential groove 116 like groove 58 is formed in plug 72 coincident with passage 112a and O-rings 118a and 118b are installed on the plug on opposite sides of groove 116 in order to isolate the entrance to passage 112a.

The outer or left-hand end of plug 72 has a reduced diameter at 72a for receiving a long cylindrical sleeve 122. Sleeve 122 extends through a bushing 124 secured to the distal end of shroud 14 and is exteriorly threaded at 122a to mate with corresponding internal threads formed in the neck portion 16a of tip 16. Shroud 14 and sleeve 122 are held in place by a set screw 125 turned down into a threaded passage 126 at the distal end of housing 12 with the screw end extending through an opening 128 in shroud 14 and bearing against sleeve 122.

A long, small diameter expansion tube 132 extends from passage 112 through sleeve 122 into the interior of tip 16. A second larger diameter return tube 134 extends from passage 110 in plug 72 through sleeve 122 into tip 16. These tubes conduct refrigerant to and from tip 16 as determined by the setting of knob 24 which controls the valve assembly 25.

Plug 104 at the right-hand end of valve assembly 25 is somewhat different from plug 72. It does have an axial bore 140 which is counterbored and threaded at 140a to accommodate a threaded male hose coupling 142 that terminates the hose supply line 22a inside housing 12. The exhaust line 22b in hose 22 also terminates in a threaded female coupling 146 connected to one end of a pipe 150 whose other end is connected to port 56 in manifold 34.

Referring now to FIGS. 2 and 7A to 7C, the lower portion of the knob stem 24a opposite balls 1' and 2' is profiled as shown in FIGS. 7A to 7C. More particularly, the stem has arcuate indentations or recesses 156 and 158 which are spaced apart by an angle of about 140°. As the knob 24 is turned, the balls 1' and 2' either ride on the periphery of valve stem 24a or reside in one of the recesses 156 and 158. When knob 24 is turned so that ball 1' lies on the periphery of stem 24a as shown in FIG. 7A, the ball 1', along with push rod 105 is displaced to the right sufficiently to unseat valve ball 1 from its seat 98 so that refrigerant from the supply line 22a can flow through valve structure 43 into pipe 113. On the other hand, when the knob is turned so that ball 1' rests in recess 158, the corresponding push rod 105 is shifted sufficiently to the left to permit spring 102 to seat ball 1 against its valve seat cutting off fluid flow through valve structure 43. Similarly, when the knob is turned so that ball 2' rests on the periphery of the knob stem as shown in FIG. 7B, the corresponding push rod 76 is displaced to the left sufficiently to unseat valve ball 2. On the other hand, when the knob is oriented so that ball 2' rests in recess 156 as indicated in FIG. 7A, ball 2 is seated on its valve seat 50 so that there is no fluid flow through valve structure 42.

During normal use of the instrument, once the refrigerant source 18 is turned on, refrigerant floods the supply line 22a and the bore 38 in manifold 34 to the right of valve ball 1. Assume at the outset that knob 24 is turned to the OFF position so that its stem is oriented as shown in FIG. 7B. With that setting, the ball 1' is situated in recess 158 so that ball 1 is seated on valve seat 98. Consequently, there is no fluid flow along valve structure 43.

When the doctor wishes to operate instrument 10 in the freeze mode, he turns knob 24 counter-clockwise to the position shown in FIGS. 2 and 7C. In this position, both balls 1' and 2' rest on the periphery of stem portion 24b with the result that both valve balls 1 and 2 are unseated. Refrigerant is thus able to flow from the manifold bore 38 along the axial passage in valve member 92 to passage 94. Thence the refrigerant flows along the pipe 113 to passage 112 in plug 72 and through tube 132 to the interior of tip 16. The refrigerant issuing from the end of the restricted tube 132 cools sufficiently to cool the walls of tip 16 to a temperature low enough to freeze human tissue. Refrigerant is conducted out of tip 16 by way of return tube 134. The exhausting refrigerant flows through passage 110 in plug 72 into bore 36 in the valve manifold, and through bore 48 in valve member 44 to passage 54 therein. Thence the spent refrigerant is conducted by pipe 150 to the exhaust line 22b in hose 22. As long as knob 24 is maintained in its freeze position, refrigerant will continue to be circulated through the instrument tip 16 maintaining it at the correct low temperature.

When the doctor has completed the operation and wishes to detach the instrument tip 16 from tissue, he turns knob 24 clockwise to its DEFROST position so that its stem portion 24b assumes the position illustrated in FIG. 7A. Now the ball 1' is still positioned on the periphery of the stem portion so that the corresponding valve ball 1 remains unseated. Thus refrigerant continues to flow from the inlet line 22a through the capillary tube 132 to the probe tip. However, ball 2' resides in recess 156 so that valve ball 2 is seated against the valve seat 98 so that the refrigerant escaping from the tip through tube 134 can flow no further than counterbore 48a in valve member 44. As a result, the pressure inside tip 16 quickly builds up that of the source causing the gaseous refrigerant inside the tip to condense giving up its latent heat of vaporization to the walls of tip 16. The result is that the tip 16 warms enough to separate easily from the tissue to which it was adhered during the freeze operating mode.

If the doctor determines that the procedure is not completed, he can recool tip 16 by returning knob 24 to its FREEZE position as described above. On the other hand, if he is satisfied with the results and wishes to turn the instrument off, he simply turns knob 24 to its OFF position so that its stem 24a is oriented as shown in FIG. 7B. Now the ball 1' drops into recess 158 as described at the outset so that the valve ball 1 is seated thereby interrupting the flow of refrigerant from source 18 to tip 16. Also it will be noted that ball 2' is displaced to the left so that the valve ball 2 is unseated. Consequently, refrigerant is free to vent from tip 16 through tube 134, valve structure 42 and pipe 150 to the hose exhaust line 22b.

Preferably there is provision for positively stopping knob 24 in its extreme counter-clockwise and clockwise orientations shown in FIGS. 7A and 7C. More particularly, a semi-circular groove 159 can be formed in the underside of knob 24 as shown in FIG. 2 with a pin 160 projecting up from manifold 34 extending into the groove. The position and length of groove 159 are arranged so that the pin 160 engages the opposite ends of the groove when the knob is in its FREEZE and DEFROST positions. The intermediate or OFF knob position is positively located because the ball 1' engaging in recess 158 acts as a detent that tends to retain the knob 24 in its off position.

Further, provision can be made for biasing knob 24 from its DEFROST position to its OFF position so that when the probe tip 16 is detached from the tissue, the doctor simply releases the knob which automatically returns to its OFF position thereby shutting off the instrument. This can be accomplished, for example, by inserting a small coil spring segment 161 (FIG. 2) in the groove 159 adjacent the end of the groove normally engaged by pin 160 when the knob is in its defrost position. The strength and length of the spring should be arranged to bias the knob from its FIG. 7A position sufficiently toward the FIG. 7B position such that the engagement of ball 1' in recess 158 stops the knob in its OFF position will no overshoot.

Although the subject cryosurgical instrument has all of the advantages of the prior art devices above, it is further advantaged in that it does not require a console or remote foot operated valves or electrical relays or complex multiple valves. Rather all of the required valving is located in one assembly right in the handle of the instrument itself. As best seen in FIGS. 2 and 3, the valve assembly in the present instrument has an extremely compact unitary in-line construction that accomplishes all the required routing of refrigerant through the instrument in its various operating modes. Yet it still can be contained in a minimum volume so that the overall instrument has a slim profile and has excellent balance in speculum.

The changing of the tip 16 on the instrument is accomplished simply by unscrewing the tip from the sleeve 122. As noted previously, this is done when knob 24 is in the OFF position and the interior of the tip is at atmospheric pressure.

The assembly of the instrument can likewise be accomplished most expeditiously even by relatively inexperienced personnel. The parts of the valve assembly are simply arranged as shown in FIG. 3 with the ends of the pipe 113 being brazed to ports 96 and 114 and with the end of pipe 150 being brazed to port 56. The components of the valve structures 42 and 43 are inserted into opposite ends of the manifold 34 in the order shown, with the plugs 72 and 104 being held in place by the illustrated set screws. The capillary tubes 132 and 134 are brazed into the passages 112 and 110 beforehand and the end of the sleeve 122 is similarly secured to the reduced diameter plug portion 72a.

The plastic housing 12 is conveniently made in two sections 12a and 12b. When assembling the instrument, the sleeve 122 and valve assembly 25 are inserted into the housing section 12a from the right-hand end thereof. When those components are properly seated, the set screw 125 is turned down thereby retaining those components in place within the housing section 12a. Next, the knob 24 is inserted into manifold passage 35a by spreading apart balls 1' and 2' and the screw 82 is installed to retain the knob.

After the hose couplings 142 and 144 on the one hand, and 146 and 148 on the other have been connected, the housing section 12b is engaged over the reduced diameter right-hand end of section 12a and retained in place by any suitable means such as the set screws 162 shown in FIG. 2. As the instrument is easily assembled, so it can easily be disassembled for repair or replacement of parts simply by reversing the above procedure.

Certain modifications may be made to the basic in-line valve assembly 25 so that it can be actuated in different ways. For example, FIG. 8 depicts a valve assembly similar to the one shown in FIG. 2. However, instead of operating the valve balls by means of a rotary knob, a thumb wheel segment is used which is moved in a direction along the probe. The elements of the FIG. 8 valve assembly corresponding to those in the assembly shown in FIG. 2 carry the same identifying numerals. Only the different elements will be described in detail.

In the FIG. 8 embodiment, the balls 1' and 2' are not required. Rather the inner ends of the push rods 76 and 105 engage opposite ends of a rack 202. Rack 202 is slidably mounted in the central portion of manifold bore 38 which is appropriately shaped. A spur gear segment 204 is positioned in a slot 206 in the top wall of manifold 34 so that its teeth engage those of rack 202. Segment 204 is pivotally connected to the manifold by a pin 207 extending through the spur gear segment and the side walls of slot 206. Integral with segment 204 is a thumb wheel segment 208 which projects from the top of slot 206. When the instrument is fully assembled, that segment also projects from the top of housing 12 so that it can be turned by the doctor handling the instrument.

When the thumb wheel 208 is in the FREEZE position as specifically illustrated in FIG. 8, rack 202 is centrally positioned so that both valve balls 1 and 2 are unseated. Accordingly refrigerant is free to flow to and from the probe tip 16 as described previously. When the thumb wheel is urged forward, i.e., counter-clockwise in FIG. 8, the rack 202 is shifted toward the right so that valve ball 1 remains unseated while valve ball 2 is seated. Consequently refrigerant is still able to flow to the probe tip 16 through capillary tube 132 (FIG. 1).

However, there is no flow passage from the tip to the atmosphere through valve structure 42. Consequently the pressure builds up in tip 16 resulting in condensation of refrigerant and warming of the tip as described above. Finally when the thumb wheel 208 is moved rearwardly, i.e. clockwise in FIG. 8, rack 202 is shifted to the left sufficiently to seat valve ball 1 and unseat valve ball 2. Consequently the supply of refrigerant to the probe tip by way of valve structure 43 is interrupted while the refrigerant already in the tip is vented to the atmosphere by way of valve structure 42 and pipe 150.

FIG. 9 illustrates still another valve assembly which has all of the advantages of those described in connection with FIGS. 2 and 8. Here the instrument is controlled by means of a joy stick 210 which projects through an opening 212 in the top wall of manifold 34 (and also through housing 12). The inner end of joy stick 210 is connected to a cylinder 214 which is rotatable and slidable in the manifold bore 38. The opposite ends of cylinder 214 are engaged by the push rods 76 and 105. When the joy stick 210 is moved along the instrument, cylinder 214 and the push rods are shifted to unseat one or another of the valve balls 1 and 2.

Preferably the opening 212 is specially shaped in order to fix the three operative positions of joy stick 210. FIGS. 9A to 9C depict an opening 212 that is generally triangular in shape with each corner of the triangle corresponding to an operative setting of the joy stick that turns the instrument off, or places it in its freeze or defrost mode of operation.

FIGS. 9D to 9F illustrate an opening 212 having lobes which establish the proper operative positions of the joy stick 210.

In those instances where it is desirable to have an instrument handle 12 that is shorter than the one depicted in FIG. 1, it is possible essentially to fold the FIG. 2 valve assembly so that it occupies less longitudinal space. This arrangement has an added advantage for some applications because the control knob for the instrument can be located at the proximate end of handle 12, the hose 22 entering the housing through the side. A valve assembly of this type shown generally at 220 in FIGS. 10A and 10B.

Assembly 220 comprises a generally cylindrical valve manifold 222 having a pair of spaced-apart longitudinal bores 224 and 226. Both bores have reduced diameter portions 224a and 226a at their right-hand ends forming internal shoulders 228 and 230. Valve structures 42 and 43 more or less the same as those described in connection with FIG. 2 are positioned in bores 224 and 226, being seated against the shoulders 228 and 230 respectively. The elements of these structures carry the same identifying numerals as the corresponding elements in FIG. 2. A plug 232 closes the end of bore 224, being retained there by a set screw 236 turned down through the side wall of manifold 222 and engaging plug 232. A axial passage 234 in plug 232 receives a pipe 236 that is connected to the hose line 22a leading to the refrigerant source. A similar plug 238 closes off the lower bore 226, being retained and here by set screw 240. Plug 238 also has an axial passage 242 which receives the return tube 134 from tip 16. Valve structure 42 communicates via its diametric passage 54 with the capillary tube 132 leading to tip 16. The comparable passage 94 in valve structure 43 communicates with the pipe 150 connected to the hose exhaust line 22b.

The valve assembly 220 has a control knob 246 which is somewhat different from knob 24. More particularly, the knob is rotatively connected to the end of manifold 222 by a screw 248 extending through the knob and turned down into a threaded opening 250 so that the undersurface 246a of the knob faces and engages the balls 1' and 2' of the valve structures 42 and 44.

As best seen in FIGS. 10A and 10C, the radially inner portion of surface 246a that engages balls 1' and 2' is profiled to function as a cam surface for those balls. The cam profile is illustrated by the curve in FIG. 10D which shows the relative positions of the cam surface and ball 1' for the three operative positions of the knob. The knob is shown specifically in the OFF position in FIGS. 10A and 10C. It can be appreciated from FIG. 10D that in this position, placing ball 1' at 120° and ball 2' at 300°, the valve ball 1 in structure 42 is seated while the valve ball 2 in structure 43 in unseated. Consequently refrigerant from the source is unable to flow through structure 42 while the interior of the tip is vented to the atmosphere by way of return tube 134, valve structure 43 and the pipe 150 leading to the hose exhaust line 22b.

When knob 246 is turned to the FREEZE position, ball 1' is located at the peak of the cam surface on the knob (at 60°) so that the valve ball 1 in structure 42 is unseated. Ball 2' being displaced 180° from ball 1' is also located on a peak (at 240°) with the result that valve ball 2 in structure 43 is also unseated. With both valves open, refrigerant flows through structure 42 and the capillary tube 132 to tip 16. The return flow from the tip passes through tube 134 and valve structure 43 to the atmosphere.

When the knob 246 is turned to the DEFROST position, reference to FIG. 10D shows that the valve ball 1 in structure 42 is unseated while the valve ball 2 in structure 43 is seated so that while refrigerant can enter the probe tip 16 there is no return flow from the tip. The resultant pressure build-up therein causes the gaseous refrigerant to condense and thereby warm the tip walls as described previously.

The FIG. 10A valve assembly has all of the advantages of the FIG. 2 assembly in terms of size, ease of manufacture and reliability. Furthermore it also has a minimum number of parts and can be assembled or repaired easily by relatively unskilled personnel.

Figure 11A:
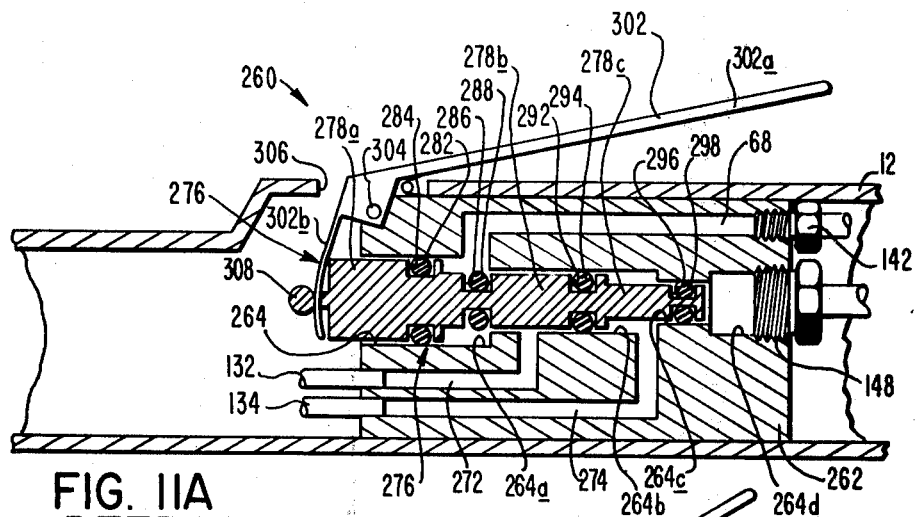
FIGS. 11A to 11C are fragmentary sectional views showing still another valve assembly embodiment for use in instruments of this type.
Figure 11B:
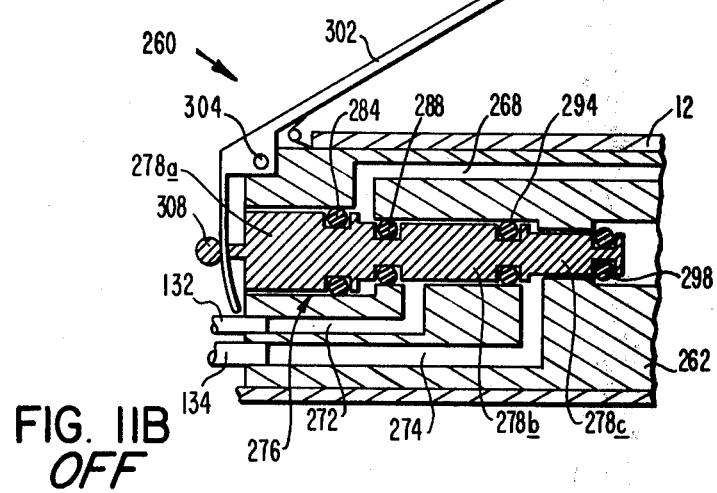
Figure 11C:
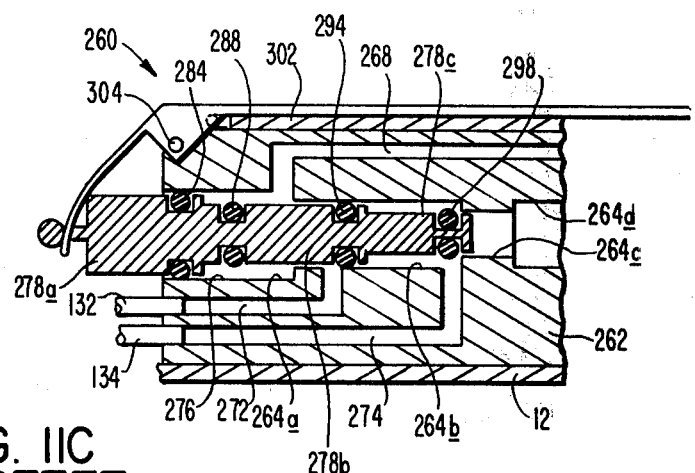

Still another in-line valve assembly suitable for controlling a cryosurgical instrument 10 is depicted generally at 260 in FIGS. 11A to 11C. Here again, the assembly has a unitary in-line construction that enables it to fit entirely within the handle 12 of the instrument. This assembly performs the same control function but differs from the others described so far in that it is lever actuated so that it is particularly suitable in those applications where a fingertip control is desired right at the distal end of the instrument handle.

Assembly 260 comprises a valve manifold 262 which has a lengthwise bore 264 whose diameter decreases in a stepped fashion from end to end. There is a relatively large diameter bore section 264a at the distal or left-hand end of the manifold. Mid-way along the manifold there is a smaller diameter bore section 264b followed by a still smaller diameter section 264c. The proximate or right-hand end section of the bore 264d has a diameter comparable to that of section 264b. Further the extreme right-hand end of section 264d is threaded to accommodate exhaust hose coupling 148 described in connection with FIG. 2. Manifold 262 is formed with an inlet passage 268 extending from the right-hand end of the manifold to the right-hand end of bore section 264a.

A hose coupling 142 installed at the end of passage 268 is connected to the refrigerant supply line 22a.

A second passage 272 extends from the left-hand end of the manifold to bore section 264b at a point of about one quarter of the way along its length. The outer end of passage 272 communicates with the capillary tube 132 leading to the tip of the instrument. A third passage 274 is formed in the manifold extending from the left-hand end thereof to the extreme right-hand end of bore section 264b. This passage communicates with the return tube 134 extending from the probe tip 16.

The bore 264 is arranged to slidably receive the stepped valve structure shown generally at 276. Structure 276 consists of a train of generally cylindrical valve members 278a, 278b 278c having progressively smaller diameters so that each member has a snug sliding fit within bore sections 264a, 264b and 264c respectively.

Valve member 278a has a circumferential groove 282 at its right-hand end accommodating an O-ring 284. A similar groove 286 containing an O-ring 288 is located near the left-hand end of valve member 278b. A similar groove and O-ring 292 and 294 are located at the right-hand end of member 278b. Finally, still another groove and O-ring pair 296 and 298 is present at the right-hand end of valve member 264c. The valve structure 276 is moved by means of a generally L-shaped lever 302 which is pivotally connected at its corner to the left-hand end of manifold 262 by a pin 304. The long leg 302a of the lever projects through a slot 306 in the wall of housing 12 while its short leg 302b is connected to a boss 308 projecting from the end of valve number 278a.

FIGS. 11A to 11C illustrate the positions of the valve structure 276 for the three operative positions of the lever 302. As seen from these figures, the entrances to the various passages in the valve manifold are positioned along the manifold such that when the lever is in its uppermost position shown in FIG. 11B, passage 268 connected to the refrigerant source is isolated from passages 272 and 274 whereby there is no refrigerant flow to the probe tip. On the other hand, the valve member 278c is displaced sufficiently to the right to establish communication between bore sections 264c and 264d. Resultantly, refrigerant is able to flow from the tip 16 through passage 274 to bore section 264d and thence to the instrument's exhaust line.

When the lever 302 is in its lowest or FREEZE position shown in FIG. 11C, the valve member 278b is shifted sufficiently to the left to establish communication between the refrigerant inlet passage 268 and the passage 272 communicating with tube 132 extending to the probe tip. Likewise valve member 278c is shifted sufficiently to the left to establish communication between passage 274 communicating with the return line 134 from the tip and bore section 264d connected to the instrument's exhaust line. Finally, when the lever 302 is in its intermediate or DEFROST position shown in FIG. 11A, the valve structure is positioned so as to connect the inlet passage 268 and passage 272 leading to the tip. However, the return passage 274 is isolated from bore section 264d by O-ring 298 so that there is no refrigerant exhaust. The resultant pressure buildup in the probe tip thereupon warms the tip as described above.

In this embodiment, like the others described previously, it is desirable to provide appropriate detents to define the three unique operative positions of the control lever or knob.

The instrument embodiments described thus far warm the tip by blocking the exhaust of refrigerant from the tip. Warming of the tip can also be achieved by routing refrigerant through the unrestricted return tube 134 from the tip. FIGS. 12A to 12C show a valve assembly for incorporation into instrument 10 that is capable of doing just that. This embodiment is quite similar to the FIG. 11 assembly. It differs in that the valve manifold is extended to the left so that the bore section 264a is longer. Further the inlet passage 268 has a branch 268a which communicates with bore section 264a at a point to the left of the connection thereto by the main passage 268. Also the return passage 274 has a branch 274a which connects to bore section 264a about a third of the way along the length thereof. In addition, the valve member 278a is longer, being extended appreciably to the left in FIGS. 12A to 12C. Furthermore a pair of spaced-apart circumferential grooves 320 and 322 containing O-rings 324 and 326 respectively, are located near the left-hand end of valve member 278a. An appropriately shaped finger actuated lever 302 is pivotally mounted on the manifold with its short leg connected to the end of valve member 278a as before.

When the lever 302 is positioned so that the instrument is off as shown in FIG. 12B, the entrance to passage 268 is isolated between O-rings 284 and 288 and the mouth of branch passage 268a is isolated between O-rings 284 and 326. Consequently refrigerant from the source cannot flow through the valve assembly to the probe tip. On the other hand, the return passage 274 is in communication with bore section 264d so that the probe tip is vented. It should be noted that the entrance to the branch passage 274a is isolated between O-rings 324 and 326 so that refrigerant cannot vent directly from the instrument itself and possibly produce a hissing sound that could then startle the doctor or patient.

When the lever 302 is fully depressed as in FIG. 12C, the instrument operates in its freeze mode. Now both the inlet passage 268 and the branch passage 268a are in communication with passage 272 leading to the probe tip. Likewise the return passage 274 is in communication with the bore section 264d leading to the instrument's exhause line so the refrigerant is free to flow through the tip. In this condition, the entrance to branch passage 274a is still isolated between O-rings 284 and 326 for the reason given above.

Finally when the lever 302 is partially depressed as shown in FIG. 12A, the instrument operates in its defrost mode. Now the valve members are positioned so that passage 268 is in communication with passage 272 while passage 274 is isolated from the bore section 264d. Thus pressure builds up in the probe tip 16 through the restricted inlet tube 132 leading to the tip. Moreover in this position of lever 302, the branch passage 268a containing refrigerant at the source pressure is in communication with the branch passage branch 274a connected to the unrestricted return tube 134 extending into the tip. Consequently refrigerant under the full source pressure immediately floods the tip through tube 134 resulting in rapid warming of the tip.

Since the pressure build-up in the tip is primarily by way of the unrestricted return line 134, if desired, the direct connection between the inlet passage 268 and the right-hand end of bore section 264a can be eliminated without any great sacrifice in the speed with which the tip becomes warmed.

The instrument embodiments specifically described above warm the instrument tip by blocking the exhaust of refrigerant from the tip to achieve a pressure buildup therein. It should be understood, however, that the basic compact in-line valve assembly construction described herein can also be employed in instruments that warm the tip by reversing the flow of refrigerant through the instrument so that the source refrigerant which is at room temperature floods the tip and thereby warms it. The valve assembly for an instrument such as this is shown generally at 340 in FIG. 13.

This unit is somewhat similar to the one shown in FIG. 9, its opposite sides being mirror images of one another. It includes a generally cylindrical manifold 342 having an axial bore 344 containing four valve structures indicated generally at 346, 348, 352 and 354. Each of these structures is essentially the same as structures 42 and 43 described in FIG. 9. Assembly also has the joy stick 210, profiled opening 212 and cylinder 214 shown in FIG. 9, the cylinder being slidable along the reduced diameter central portion of bore 344 to move the push rods 76 and 105 in one direction or the other in the same manner described in connection with FIG. 9.

A spacer plug 356 is positioned in bore 344 between valve structures 346 and 348. The plug has a diametric passage 358 which is aligned with a port 360 in the manifold wall. The plug also has an axial passage 362 which accommodates a push rod 364 whose opposite ends engage valve ball 3 in structure 346 and valve ball 4 in structure 348. The push rod 364 includes a lost motion connection at 364a which has enough play to allow valve ball 4 to be unseated by push rod 76 without that motion being transmitted so as to unseat ball 3. In addition, manifold 342 has ports 363 and 366 opposite the mouths of the diametric passages in structures 346 and 348 respectively.

Another plug 368 having similar diametric and axial openings is positioned in the bore between valve structures 352 and 354. A push rod 370 identical to push rod 364 extends through the plug and its opposite ends engage valve balls 5 and 6 in valve structures 352 and 354. Push rod 370 also has a lost motion connection 370a to permit the balls 5 and 6 to unseat independently. In addition, the manifold 346 is provided with a port 372 opposite the mouth of the diametric passage through plug 368 and ports 373 and 374 opposite the like passages in valve structures 352 and 354 respectively. The axial passages through the plugs 375 and 376 at the opposite ends of the manifold are interconnected by a pipe 377 that leads to the refrigerant source 18. The various ports in the manifold communicate with the various tubes in the instrument as indicated in FIG. 13.

Figure 13:
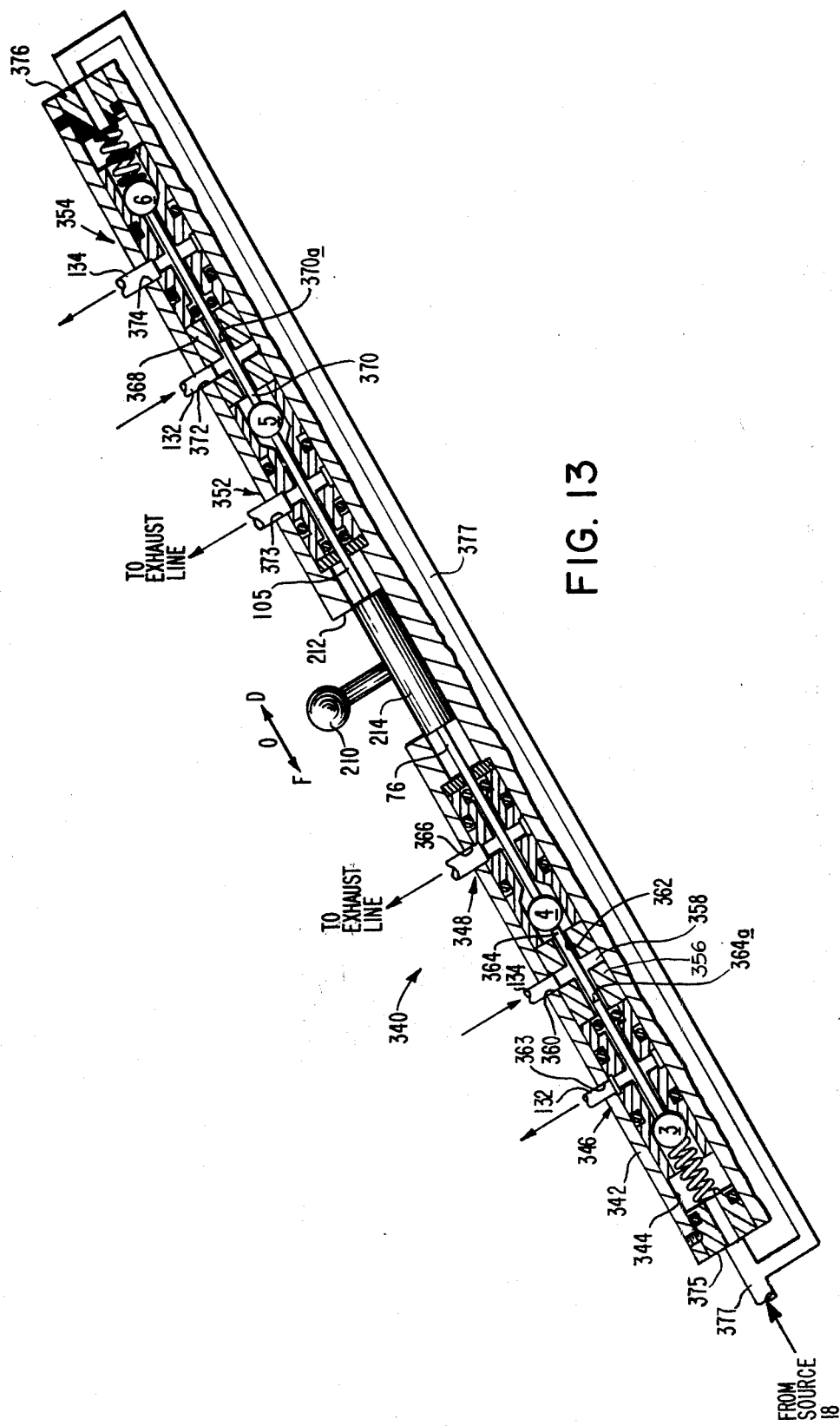
FIG. 13 is a view similar to FIG. 8 of a further assembly embodiment.

When the handle 210 is in the OFF position shown in FIG. 13, the valve balls 3 and 6 are both seated so that there is no refrigerant flow from pipe 377 through either valve structure 346 or valve structure 354. On the other hand, valve balls 4 and 5 are unseated so that ports 360 and 372 communicating with the tubes 132 and 134 extending into the probe tip 16 connect to manifold ports 366 and 373 leading to the instruments exhaust line 22b. Consequently, when the instrument is in its off position, the interior of the tip is at atmospheric pressure so that the tip can be changed if need be.

When the control stick 210 is shifted forwardly or to the left in FIG. 13, the instrument operates in its freeze mode. In this position, the valve balls 3 and 4 are unseated while the valve balls 5 and 6 are seated. Consequently the refrigerant flows from pipe 377 through valve structure 346 to port 363 connected to the tube 132 leading to the probe tip. The return flow from the tip is by way of the return tube 134, manifold port 360, through valve structure 348 to the port 366 leading to the exhaust line.

When the stick 210 is shifted rearwardly or to the right in FIG. 13, the instrument operates in its defrost mode. In this position, the balls 3 and 4 are seated while the balls 5 and 6 are unseated. Consequently room temperature refrigerant present in pipe 377 flows through valve structure 354 to the manifold port 374 connected to the unrestricted return tube 134 leading to the probe tip. The return flow of refrigerant from the tip is by way of tube 132 connected to port 372, valve structure 352 and the port 373 leading to the exhaust line. The warm refrigerant flooding the tip 16 and flowing continuously through it quickly warms the tip surfaces to a temperature permitting the separation of the tip from frozen tissue.

Assembly 340 has in common with the other assemblies described above the advantages of ruggedness and reliability. Yet it still has a relatively few number of moving parts considering all the functions it performs. Furthermore it is easily assembled with many identical parts so that the cost of making an instrument incorporating that assembly is kept to a minimum.

It should be understood that structural modifications can be made in the FIG. 13 assembly. For example, if the innermost valve structures 348 and 352 are turned around, the lost motion connections 364a and 370a can be eliminated, provided the connections of the expansion tube 132 and return tube 134 to the manifold 342 are reversed. Now when the stick 210 is in its OFF position, valve balls 3 and 6 are seated and balls 4 and 5 are unseated as before. When the stick is in FREEZE position, balls 3 and 5 are open permitting the source refrigerant to flow through valve structure 346 to the probe tip 16 via expansion tube 132 now at port 360. Fluid leaves the tip through the return tube 134 now connected to port 373 and flows through valve structure 352 to the exhaust line. At this point balls 4 and 6 are closed so that there is no fluid flow through structures 348 and 354.

In the defrost mode of operation, the valve balls 4 and 6 are unseated, while balls 3 and 5 are seated. Consequently the refrigerant flow is through valve structure 354 to the return tube 134 leading to the probe tip. The return flow is by way of the expansion tube 132 now connected to manifold port 360. Thence the refrigerant flows through valve structure 348 to the exhaust line.

Figure 14B:
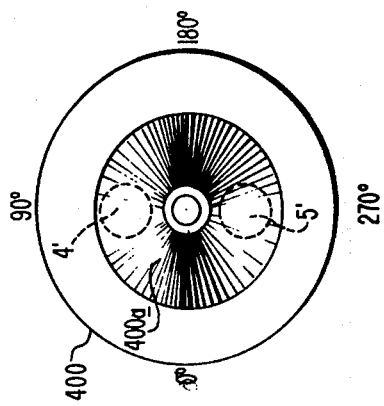
FIGS. 14A to 14C are views similar to FIGS. 10A, 10C and 10D of another embodiment.
Figure 14A:
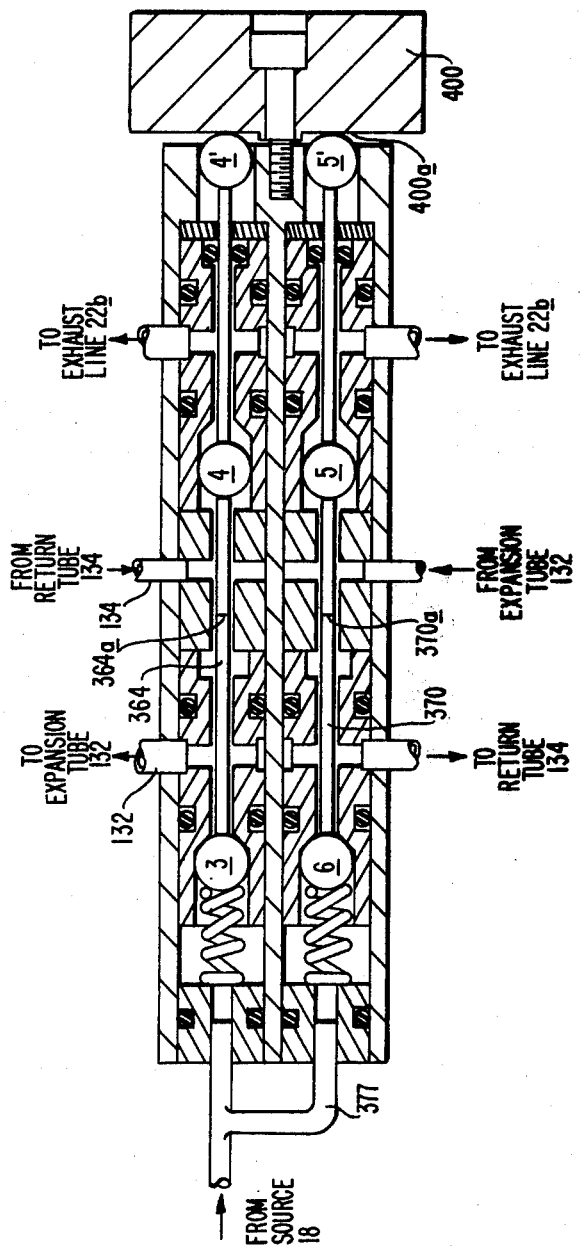
Figure 14C:
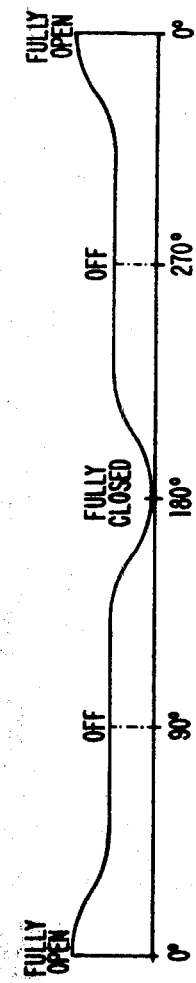

The FIG. 13 valve assembly can also be folded much like the assembly depicted in FIG. 9 so that it has less linear extent. A folded valve assembly such as this is illustrated in FIG. 14A. The assembly is controlled by a cam knob 400 rotatively connected to the proximate or right-hand end of the manifold. The inner surface 400a of the knob cams against a pair of balls 4' and 5'. The movement of ball 4' controls the opening and closing of valve balls 3 and 4 while the movement of ball 5' controls balls 5 and 6. The cam surface 400a is illustrated in FIG. 14B and the cam profile is indicated by the graph in FIG. 14C, with the position of the ball 4' shown in relationship to the graph. In all respects this construction has the same advantages as the others with respect to ruggedness, reliability and ease of assembly and maintenance.

Figure 15:
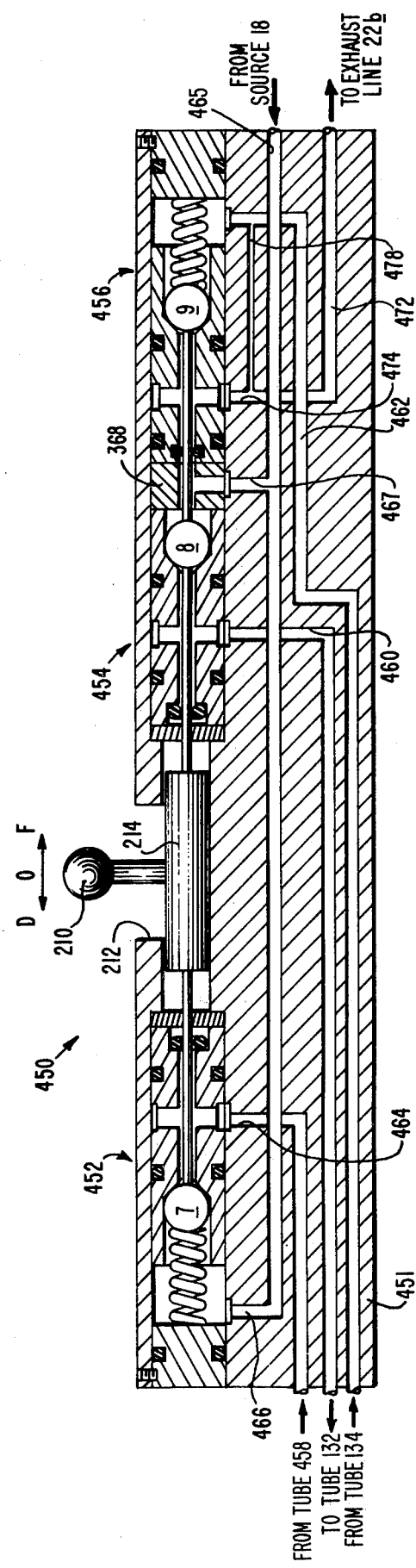
FIG. 15 is a view similar to FIG. 8 of another assembly made according to this invention.

The subject valve assembly can also be used to control an instrument whose tip 16 is warmed by flooding the tip with room temperature refrigerant through a large diameter flow tube separate from the usual expansion and return tubes leading to the tip like the one in the last mentioned patent above. An arrangement for an instrument such as this is shown generally at 450 in FIG. 15, with its relationship to the probe tip 16 being indicated diagrammatically.

Assembly 450 has a valve manifold 451 similar to the one illustrated in FIG. 13. However the manifold only contains three valve structures shown generally at 452, 454 and 456. These include valve balls 7, 8 and 9 respectively. As is the case with instruments of this type, in addition to the usual expansion tube 132 and return tube 134 extending into the tip 16, there is a third large diameter tube 458 through which room temperature refrigerant is conducted during the defrost mode of operation. Tube 132 is connected to port 460 adjacent structure 454, tube 134 leads to port 462 adjacent structure 456 and tube 458 connects to port 464 at structure 452. Refrigerant from the source is supplied to a passage 465 leading to port 466 at valve structure 452 and to port 467 adjacent spacer plug 368 between structures 454 and 456. Refrigerant exhausts from the manifold by way of a passage 472 having a port 474 adjacent valve structure 456.

Assembly 450 is controlled by joy stick 210 whose three operative positions are determined by the profiled opening 212 through which it projects. When the stick is its central OFF position shown in FIG. 15, all three valve balls 7, 8 and 9 are closed so that there is no refrigerant flow to tip 16. When the stick is shifted to the right to its FREEZE position, balls 8 and 9 are unseated so that refrigerant flows through valve structure 454 to the tip 16 via expansion tube 132. The return flow from the tip is by way of return tube 134 and valve structure 456 to the exhaust line. At this time, valve ball 7 remains seated so that there is no refrigerant flow through valve structure 452.

When the stick 210 is moved to the left to its DEFROST position, valve ball 7 is unseated so that room temperature refrigerant flows through valve structure 452 to the tip 16 by way of the large diameter tube 458. At this point, balls 8 and 9 are seated so there is no return flow of refrigerant from the tip. Consequently the pressure in the tip builds up immediately causing the refrigerant to condense resulting in rapid warming of tip 16.

It should be mentioned at this point that it is desirable to provide a small diameter bleed line 478 between ports 462 and 474 to allow a slight flow of refrigerant from tip 16 to prevent liquid buildup in the tip during the defrost mode of operation and also to relieve pressure from the tip when the instrument is in its off position.

Figure 16:
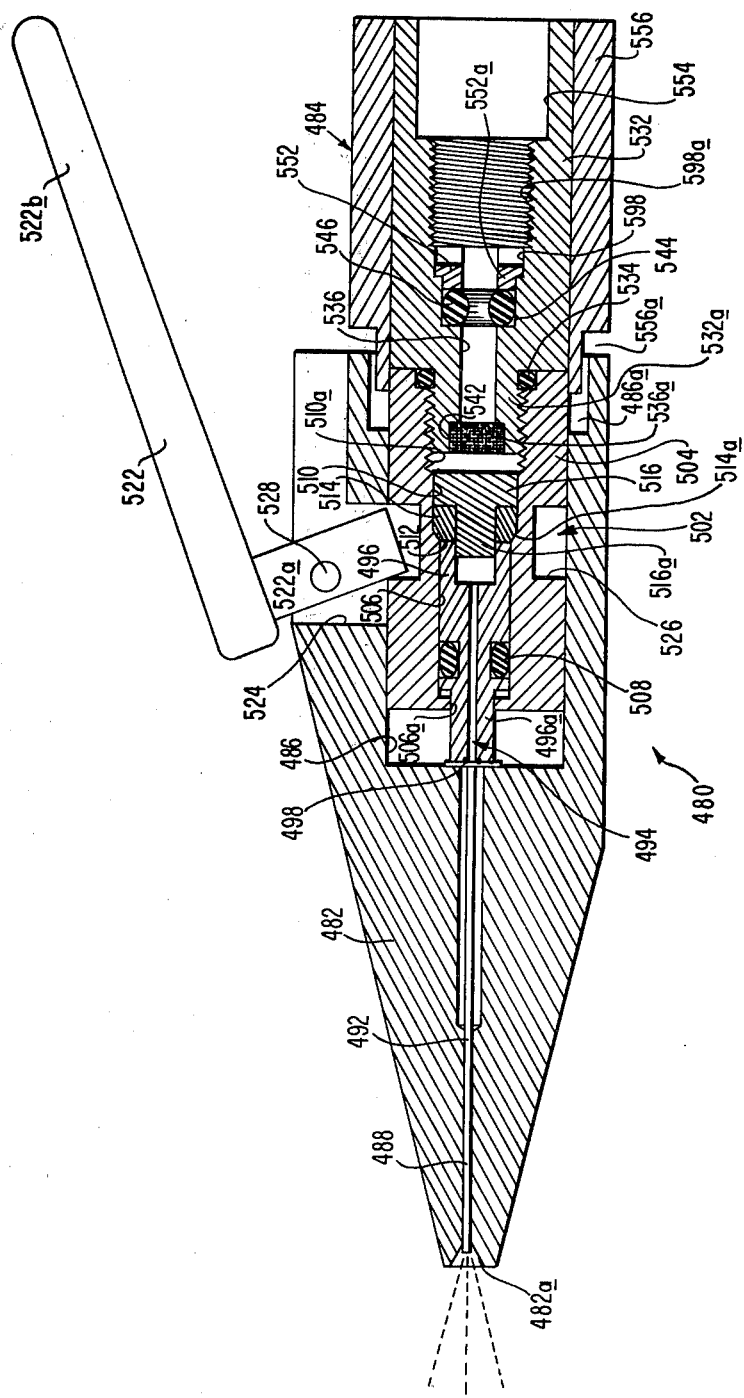
FIG. 16 is a spray tip for the FIGS. 1 and 2 instrument.

Referring now to FIG. 16, the present probe is particularly suitable for use by those medical personnel who have occasion to use such probes for different purposes. This is because when the instrument is turned off as described above, the tip becomes depressurized. Thus the tip 16 illustrated in FIG. 2 is easily removed simply by unscrewing it from the threaded end 122a of sleeve 122. Whereupon a spray tip shown generally at 480 in FIG. 16 can be turned down onto sleeve end 122a.

In some cases it may also be desirable to have the tip 480 closer to the handle 12 so that the user can more accurately direct the refrigerant spray from the instrument's tip. This is a simple matter of separating the sleeve 122 and plug 72 from the probe handle by loosening screws 74a and 74b. Then a shortened version of the sleeve may be substituted.

The spray tip 480 includes a generally conical housing 482 made of a suitable impact resistant plastic and a generally cylindrical adapter 484 threaded into housing 482. Housing 482 is formed with a relatively large diameter axial bore 486 that extends from its wide end approximately half-way along its length. A very small diameter axial passage 488 extends from the bottom of bore 486 to the pointed end of housing 482 which is conically recessed at 482a. Passage 488 contains a small diameter capillary tube 492 having an internal diameter on the order of 0.008 inch. Tube 492 extends from the recess 482a into bore 486 where it is received in an axial passage 494 in a generally cylindrical plunger 496 positioned in bore 486. The capillary tube 492 is brazed to the interior end of plunger 496 at 498 so that there can be no fluid flow along the passage 494 in the plunger.

Housing bore 486 also contains a generally cylindrical, slidable valve assembly shown generally at 502. Assembly 502 includes a cylindrical shuttle 504 snugly but slidably received in bore 486. Shuttle 504 has an axial bore 506 for slidably receiving plunger 496. The outer end of bore 506 has a reduced diameter section 506a for accommodating a reduced diameter portion 496a of the plunger. Also an O-ring 508 seated in a groove in the plunger 496 provides a sliding seal between the plunger and the shuttle 504.

The shuttle bore 506 is counterbored at 510 and the shoulder between bores 506 and 510 is tapered to provide a conical valve seat 512. An annular valve member 514 has a tapered edge 514a which is arranged to seat on the valve seat 512. The valve member 514 is slidably received in the counterbore 510 along with a discoid plug 516 which projects through the central opening in valve member 514 and into a bore 518 in the adjacent end of plunger 496 so that it axially guides the movements of valve member 514 and plug 516 in the counterbore 510.

The outer portion of counterbore 510 is threaded at 510a in order to receive the adapter 484. However ample clearance is provided between the inner end of the adapter and plug 516 to permit sufficient axial displacement of the plug 516 to unseat the valve member.

The valve member is unseated by a finger actuated L-shaped lever 522 whose short leg 522a extends through a slot 524 in housing 482 and projects into an annular groove 526 in shuttle 504. The short leg 522a of the lever 522 is pivotally connected to the housing by a pivot 528 extending through the leg 522a into the opposite side walls of slot 524. The long leg 522b of the lever extends back an appreciable distance from the tip end so that it can be pressed conveniently by the operator's index finger.

The adapter 484 consists of a generally cylindrical metal block 532 having a reduced diameter threaded end 532a that is turned down into the counterbore 510 as noted above. An O-ring 534 encircling the threaded portion end at its base provides a fluid tight fit between the block 532 and shuttle 504.

Block 532 has an axial bore 536 whose inner end is counterbored at 536a to accommodate a discoid sintered bronze filter plug 542. The opposite end of bore 536 is also counterbored to provide three axial bore sections having progressively smaller diameters proceeding inward. The innermost, smallest diameter section 544 contains an O-ring 546 which constrains tubes 132 and 134 (FIG. 2) when the tip is connected to the probe handle. The next largest section 548 is threaded at 548a and a collet 552 is seated at the bottom of that section with its neck projecting into section 544. A central passage 552a in the collet permits fluid to pass from section 548 to section 544. The largest diameter bore section 556 receives shroud 111 (FIG. 1).

A sleeve 556 encircles the block 532 and it has a reduced diameter end portion 556a that is received into the end of housing bore 486 which is enlarged at 486a to accommodate that sleeve portion.

In operation, the spray tip 480 is connected to the threaded end 122a of sleeve 122 (FIG. 2) and knob 24 is turned to the FREEZE position. Liquid refrigerant under pressure immediately fills bore 536 and counterbore 510 upstream of plug 516 and tends to force the valve member 514 to its seat so that no refrigerant flows through the capillary tube 492 to the tip end.

When the doctor wants to spray tissue in order to freeze the tissue, he depresses lever 522. This movement jacks the housing 482 rearwardly (i.e. to the right in FIG. 16) relative to the shuttle 504. Since the plunger 496 is bottomed in bore 486, the plunger moves with the housing thereby unseating valve member 514. Refrigerant now flows around plug 516 and member 514 through the capillary tube 492.

When the liquid refrigerant approaches the end of the tube, the drop in pressure causes the refrigerant to vaporize so that the refrigerant actually leaves the tip end 482a as a saturated vapor spray shown in dotted lines at S whose temperature is low enough to freeze tissue.

As soon as the lever 522 is released, the pressure of the refrigerant in counterbore 510 moves plug 516 toward the left thereby reseating valve member 514 and stopping the refrigerant spray from the tip. If the doctor is finished with the instrument, he can now turn knob 24 to its OFF position and depress lever 522 thereby venting the refrigerant remaining inside the tip to the atmosphere.

We have seen from the foregoing that the improved inline valve constructions described herein allow the full control of a cryosurgical instrument by a knob or lever right on the instrument itself. Remote consoles, foot valves, relays and other accoutrements are not required. Still however the instrument as a whole is small, relatively lightweight and compact with excellent balance so that it can be used by a doctor for a long period without his becoming fatigued. Furthermore the compactness of the valve assembly permits the unit to have a long slim profile with clean lines that does not present a threatening appearance to the patient as do other more massive gun-type instruments of this general type.

Furthermore because of its in-line construction, the valve assembly and hence the instrument as a whole can be assembled quite readily by relatively unskilled personnel. By the same token, it is easily disassembled for repair and routine maintenance. Consequently the cost of obtaining and maintaining instruments of this kind is kept to a minimum.

It will thus be seen that the objects set forth above among those made apparent by the preceding description are efficiently attained, and since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described.

I claim:

1. A cryosurgical instrument comprising
   A. an elongated hollow handle,
   B. a hollow thermally conductive tip projecting from the handle,
   C. a valve assembly positioned inside the handle, said assembly including
      (1) an elongated manifold extending axially in the handle, said manifold having an upstream end and a downstream end,
      (2) at least one passage extending the length of the manifold, and
      (3) at least two substantially similar valve sections in paid at least one passage in said manifold, each said section including
         (a) a valve seat,
         (b) a movable valve member,
         (c) means for biasing the member toward said seat, and
         (d) push means extending along the manifold and having first and second ends, said first end projecting through the seat and engaging the valve member,
   D. means for supplying refrigerant to said at least one manifold passage at a point downstream in the manifold from a first valve section seat,
   E. a restrictive inlet tube extending from said manifold to the interior of said tip,
   F. a less restrictive return tube extending from the interior of the tip to the manifold at a point in a said passage upstream in the manifold from a second valve section seat,
   G. a first fluid conduit extending from said at least one passage at a point upstream from the first valve section seat to the manifold end of the inlet tube,
   H. a second fluid conduit extending from said at least one passage at a point therein downstream in the manifold from the second valve section seat to the atmosphere, and
   I. actuating means engaging the second end of each said push means, said actuating means having a finger actuatable portion extending outside the handle for moving said actuating means between three operative positions, in one of which positions the actuating means moves the push means to unseat the valve member in the first and second valve sections, in a second of which positions the actuating means moves the push means to unseat the valve member in the first valve section while the second section valve member remains seated, and in the third of which positions the actuating means moves the push means to unseat the second section valve member while the first section valve member remains seated.

2. The cryosurgical instrument defined in claim 1 wherein
   A. the first and second valve sections are positioned at opposite ends of said at least one passage so that said second ends of the push means therein oppose one another near the center of the manifold,
   B. said actuating means is positioned in said at least one passage between said second push means ends, and
   C. said finger actuatable portion extends out of the handle intermediate the handle ends.

3. The cryosurgical instrument defined in claim 2 wherein
   A. said actuating means comprises
      (1) a cam having push means-engaging surfaces defining said three operative positions, and
      (2) means for rotatably mounting the cam in said at least one passage so that said cam can be turned about an axis substantially perpendicular to the axis of said at least one passage,
   B. said finger actuatable portion comprises a knob affixed to said cam.

4. The cryosurgical instrument defined in claim 2 wherein said actuating means comprises a rigid member slidable along said at least one passage.

5. The cryosurgical instrument defined in claim 4 wherein
   A. said rigid member is a rack, and
   B. said finger actuatable portion comprises
      (1) a pinion,
      (2) means for rotatively mounting the pinion so that its teeth engage the rack whereby when the pinion is rotated the rack slides in said at least one passage to said three positions.

6. The cryosurgical instrument defined in claim 4 wherein
   A. said finger actuatable portion comprises a joy stick, and
   B. further including means defining cam surfaces adjacent said stick for engagement by the stick to define said three operative positions.

7. The cryosurgical instrument defined in claim 1 wherein each said push means includes an elongated rod extending between a valve member and said actuating means.

8. The cryosurgical instrument defined in claim 1 and further including means for biasing said actuating means from said second position to said third position.

* * * * *

UNITED STATES PATENT AND TRADEMARK OFFICE
CERTIFICATE OF CORRECTION

PATENT NO. : 4,146,030
DATED : March 27, 1979
INVENTOR(S) : Joseph A. Holroyd

It is certified that error appears in the above-identified patent and that said Letters Patent are hereby corrected as shown below:

Col. 8, line 51, "will" should be --with--.

Col. 11, line 16, "in" (second occurrence) should be -- is --.

Col. 13, line 43, "exhause" should be --exhaust--.

Col. 13, line 58, after "Consequently", insert a comma --,--.

Col. 14, line 58, "instruments" should be --instrument's--.

Col. 16, line 28, "is its" should be --is in its--.

Col. 17, line 2, "resistent" should be --resistant--.

Col. 19, line 14, "paid" should be --said--.

Signed and Sealed this

Twelfth Day of June 1979

[SEAL]

Attest:

RUTH C. MASON
*Attesting Officer*

DONALD W. BANNER
*Commissioner of Patents and Trademarks*